(12) United States Patent
Druke et al.

(10) Patent No.: US 7,757,028 B2
(45) Date of Patent: Jul. 13, 2010

(54) MULTI-PRIORITY MESSAGING

(75) Inventors: Michael B Druke, Half Moon Bay, CA (US); Philip L Graves, San Jose, CA (US); Theodore C Walker, Portola Valley, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 178 days.

(21) Appl. No.: 11/480,282

(22) Filed: Jun. 30, 2006

(65) Prior Publication Data

US 2007/0150631 A1 Jun. 28, 2007

Related U.S. Application Data

(60) Provisional application No. 60/753,991, filed on Dec. 22, 2005.

(51) Int. Cl.
*G06F 12/00* (2006.01)
*G05B 15/00* (2006.01)
*B25J 1/00* (2006.01)
*G06F 15/16* (2006.01)

(52) U.S. Cl. .............. 710/244; 710/36; 414/1; 700/245; 700/258; 709/207; 370/235; 370/394

(58) Field of Classification Search ................. 710/244; 700/245
See application file for complete search history.

(56) References Cited

U.S. PATENT DOCUMENTS

| | | | |
|---|---|---|---|
| 5,068,851 A | 11/1991 | Bruckert et al. | |
| 5,652,711 A | 7/1997 | Vennekens | |
| 5,762,458 A * | 6/1998 | Wang et al. | 414/1 |
| 6,021,129 A * | 2/2000 | Martin et al. | 370/395.72 |
| 6,182,120 B1 * | 1/2001 | Beaulieu et al. | 709/207 |
| 6,198,971 B1 | 3/2001 | Leysieffer | |
| 6,424,625 B1 | 7/2002 | Larsson et al. | |
| 6,674,731 B1 | 1/2004 | Bradshaw et al. | |
| 6,728,599 B2 * | 4/2004 | Wang et al. | 700/258 |
| 6,760,337 B1 * | 7/2004 | Snyder et al. | 370/395.4 |
| 6,920,586 B1 | 7/2005 | Moyer | |
| 7,440,793 B2 | 10/2008 | Chauhan et al. | |
| 2002/0080719 A1 * | 6/2002 | Parkvall et al. | 370/235 |
| 2002/0181503 A1 * | 12/2002 | Montgomery, Jr. | 370/468 |
| 2003/0112758 A1 * | 6/2003 | Pang et al. | 370/235 |
| 2004/0008693 A1 * | 1/2004 | Grove et al. | 370/395.52 |
| 2004/0125825 A1 * | 7/2004 | Lym et al. | 370/519 |
| 2004/0196861 A1 * | 10/2004 | Rinchiuso et al. | 370/441 |
| 2005/0058134 A1 * | 3/2005 | Levi et al. | 370/389 |
| 2005/0132104 A1 * | 6/2005 | Brown | 710/36 |
| 2005/0199728 A1 * | 9/2005 | Schmidt et al. | 235/462.46 |

(Continued)

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

(Continued)

*Primary Examiner*—Khanh Dang
*Assistant Examiner*—Brian T Misiura

(57) ABSTRACT

Methods, systems, and computer program products for transmitting first-priority data and second-priority data. The first-priority data and second-priority data are stored in separate data buffers, and the first-priority data is transmitted preferentially over the second-priority data.

26 Claims, 6 Drawing Sheets

U.S. PATENT DOCUMENTS

| | | | |
|---|---|---|---|
| 2005/0265341 A1* | 12/2005 | Benedyk et al. | 370/389 |
| 2007/0147250 A1* | 6/2007 | Druke et al. | 370/235 |
| 2007/0147385 A1* | 6/2007 | Druke et al. | 370/394 |
| 2007/0153811 A1* | 7/2007 | Venters et al. | 370/395.62 |
| 2008/0022165 A1* | 1/2008 | McKim et al. | 714/712 |
| 2008/0159126 A1* | 7/2008 | Takagi et al. | 370/222 |
| 2009/0012532 A1* | 1/2009 | Quaid et al. | 606/130 |
| 2009/0046735 A1* | 2/2009 | Regnier et al. | 370/412 |

OTHER PUBLICATIONS 11-479160 Final Office Action mailed Oct. 14, 2008, 21 pages.
11-479160 Non-Final Office Action mailed Apr. 8, 2008, 11 pages.
11-479203 Non-Final Office Action mailed Oct. 2, 2008, 16 pages.
PCT/US06/62366 International Search Report mailed Oct. 1, 2008, 5 pages.
PCT/US06/62366 Written Opinion of the International Search Authority dated Sep. 3, 2008, 7 pages.
PCT/US06/62367 International Search Report mailed Jul. 1, 2008, 2 pages.
PCT/US06/62367 Written Opinion of the International Search Authority mailed Jul. 1, 2008, 8 pages.
PCT/US06/62372 International Search Report mailed May 8, 2008, 2 pages.
PCT/US06/62372 Written Opinion of the International Search Authority.
U.S. Appl. No. 11/479,203 Final Office Action mailed Apr. 14, 2009, 20 pages.
U.S. Appl. No. 11/479,160 Non-Final Office Action mailed Apr. 2, 2009, 27 pages.

* cited by examiner

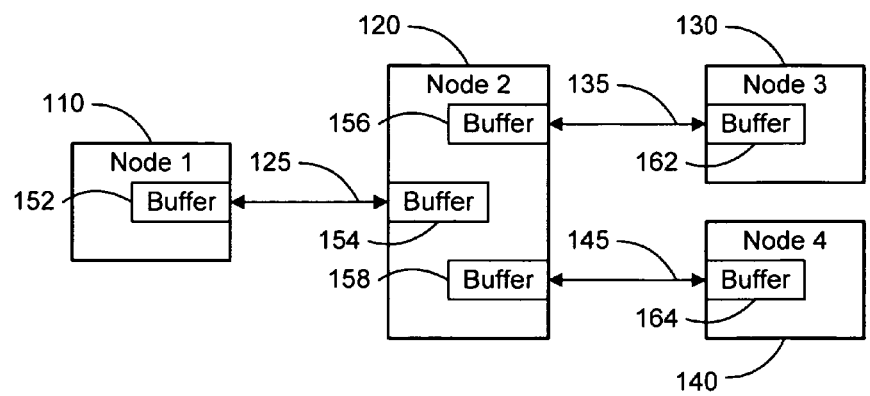
FIG._1A
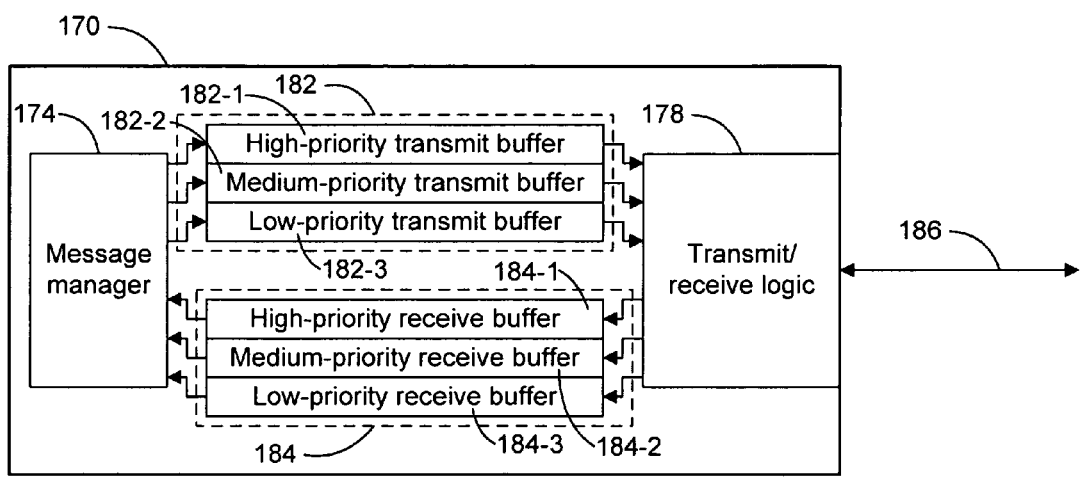
FIG._1B

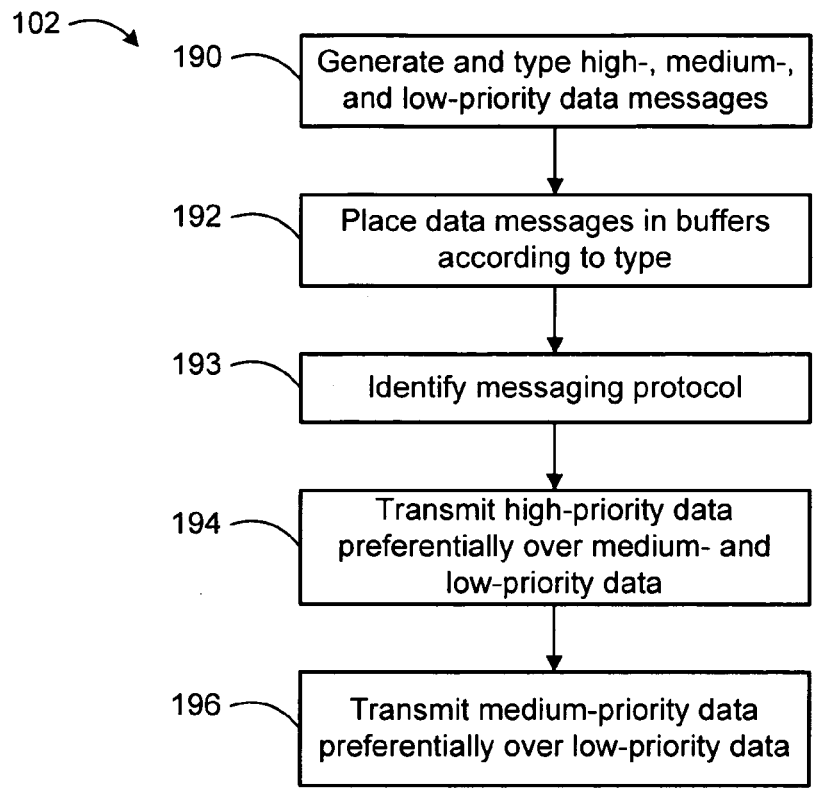
FIG._1C
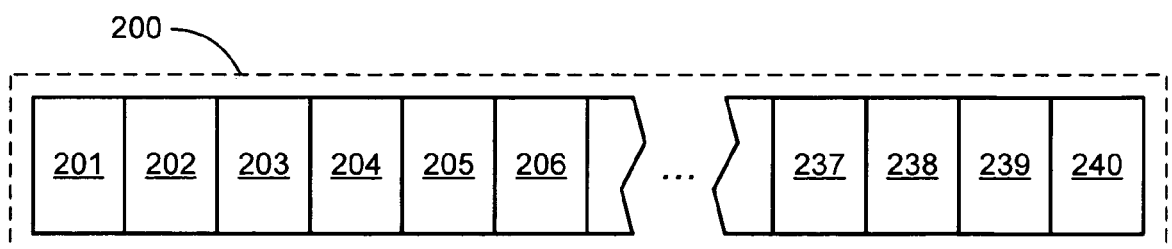
FIG._2

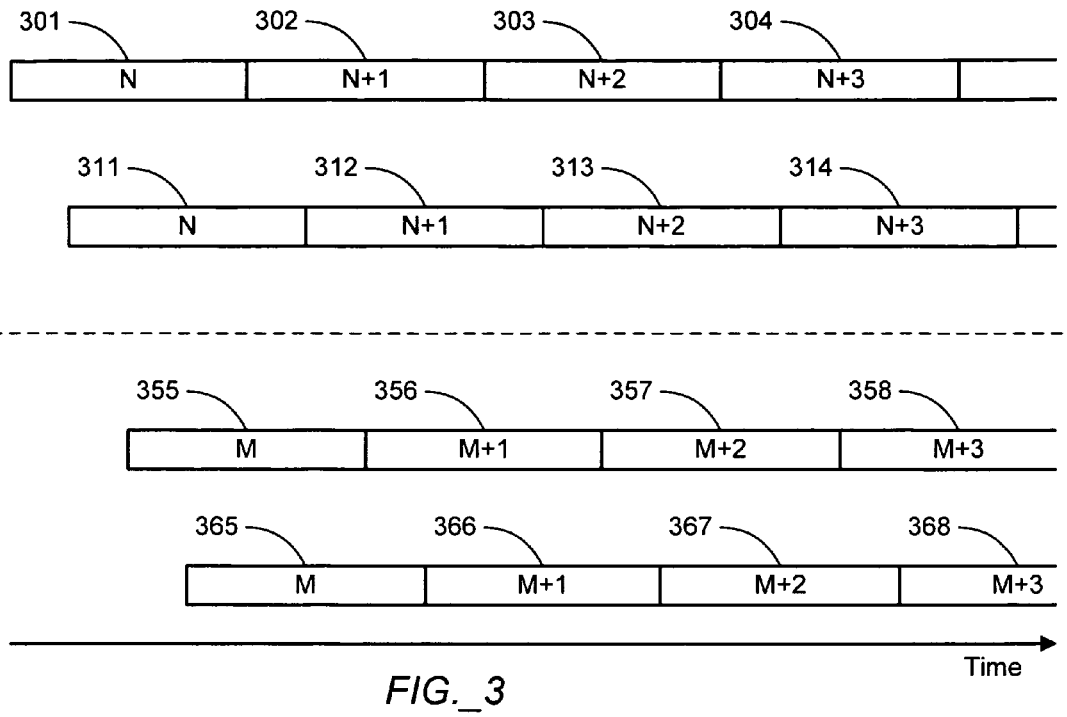
FIG._3
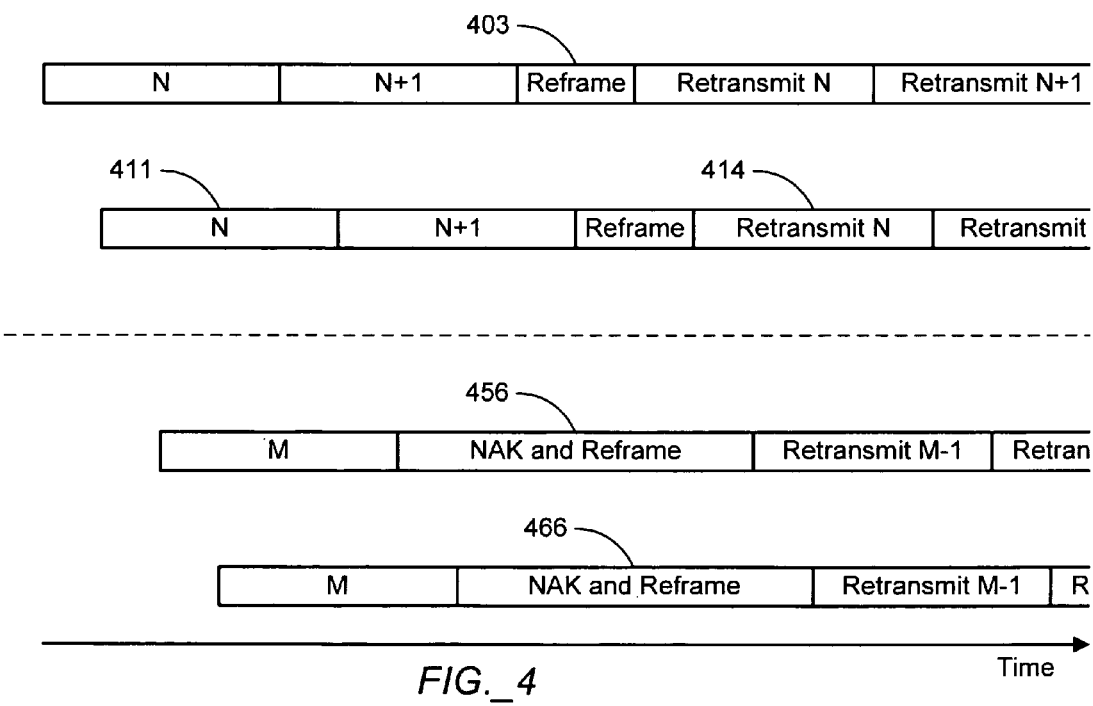
FIG._4

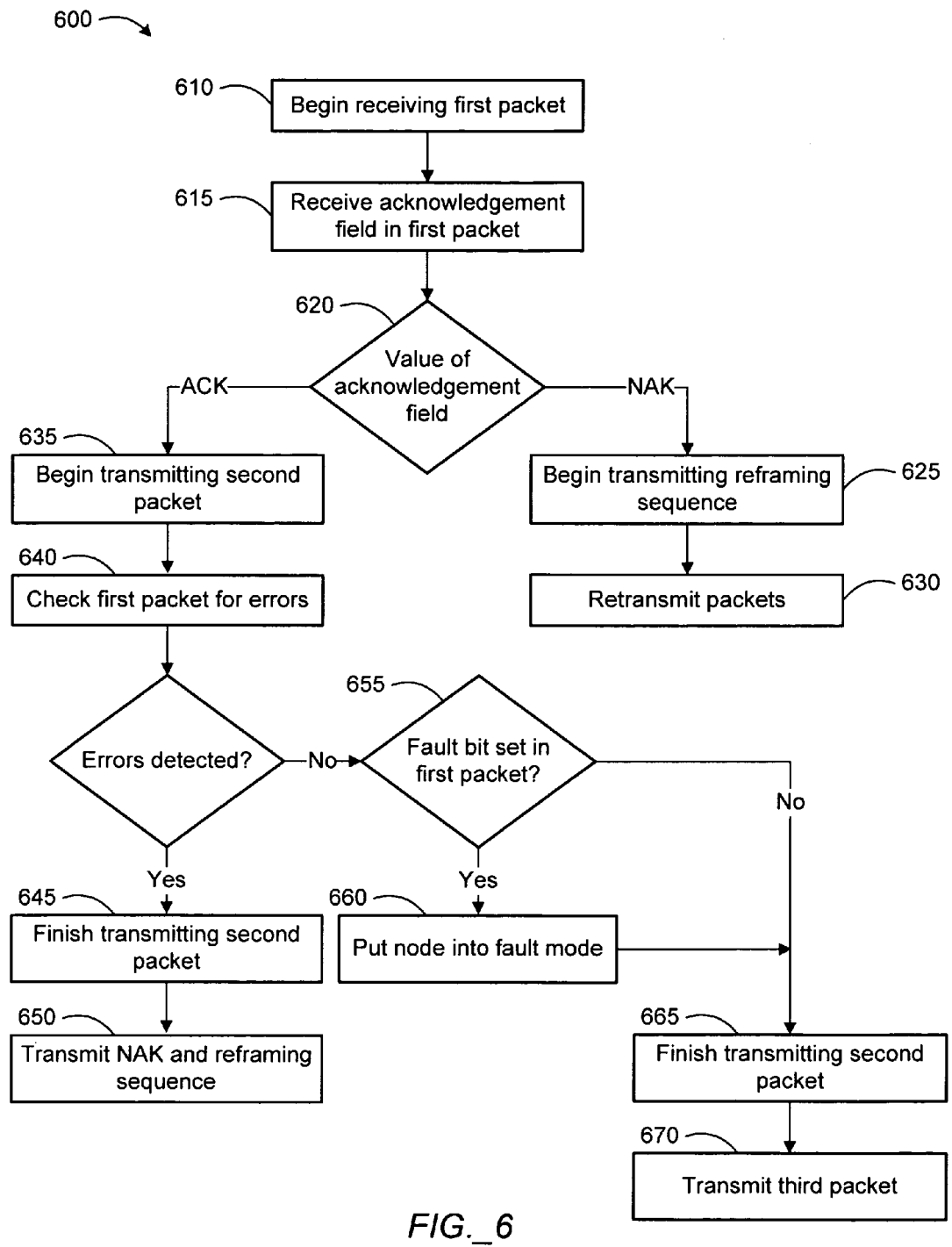
FIG._6

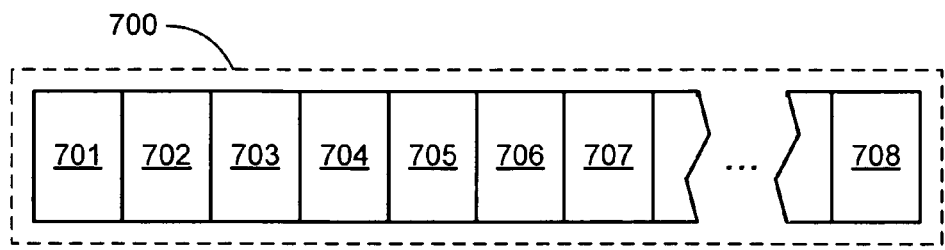
FIG._7
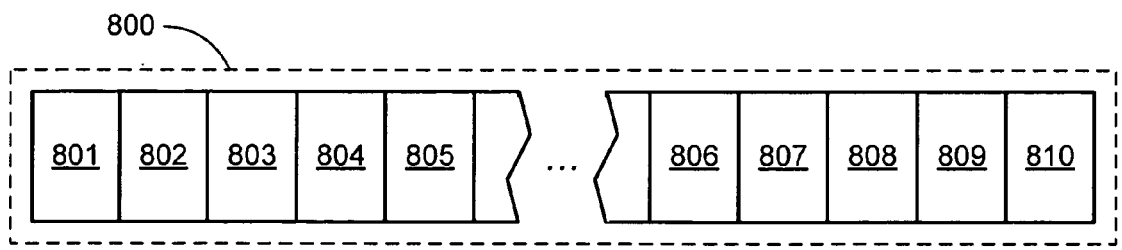
FIG._8

MULTI-PRIORITY MESSAGING

CLAIM OF PRIORITY

This application claims the benefit of U.S. Provisional Patent Application Ser. No. 60/753,991, filed on Dec. 22, 2005, the entire contents of which are hereby incorporated by reference.

BACKGROUND

The present disclosure relates to information systems.

Certain systems transmit information having various degrees of importance between system components. More important information can be given a higher priority during processing. In conventional robot-assisted surgical systems, for example, control and feedback signals typically are given a higher priority during processing. Other types of signals, such as routine system status messages, typically are given a lower priority during processing. The system typically is resilient to the delay of low-priority signals.

One conventional communication system used in robot-assisted surgical systems uses several hundred paths (e.g., wires) to connect a surgeon's control console to robotic arms. The use of hundreds of paths allows a dedicated path for each type of signal that is tailored at design time to the specific signal. However, the use of hundreds of paths makes setup and maintenance of the system cumbersome and requires substantial room to route all of the paths.

SUMMARY

In one aspect, a system is provided that includes a programmable processor operable to execute instructions and a first data buffer coupled to the programmable processor. The programmable processor transfers first-priority data to the first data buffer responsive to the instructions. The first data buffer is for use with only the first-priority data. A second data buffer is coupled to the programmable processor, and the programmable processor transfers second-priority data to the second data buffer responsive to the instructions. The second data buffer is for use with only the second-priority data. The system also includes a data link and transmission logic coupled to the first and second buffers and to the data link. The transmission logic transmits the first-priority data preferentially over the second-priority data over the data link in accordance with a messaging protocol.

Particular implementations may include one or more of the following features. The first-priority data can include commands to control the movement of a robotic arm and the second-priority data can include at least one of non-critical status information and error-logging information. A third data buffer can be coupled to the programmable processor. The programmable processor can transfer third-priority data to the third data buffer responsive to the instructions, and the third data buffer can be for use with only the third-priority data. The first-priority data can be high-priority data, the second-priority data can be low-priority data, and the third-priority data can be medium-priority data.

The messaging protocol can require that the transmission logic transmit the first-priority data from the first data buffer preferentially over the second-priority data from the second data buffer. The messaging protocol can require that the transmission logic transmit the first-priority data from the first data buffer preferentially over the third-priority data from the third data buffer. The messaging protocol can requires that the transmission logic transmit the third-priority data from the third data buffer preferentially over the second-priority data from the second data buffer. Transmitting the first-priority data preferentially over the second-priority data can include transmitting any available first-priority data before any available second-priority data. Transmitting the first-priority data preferentially over the second-priority data can include allocating more transmit slots to available first-priority data than to available second-priority data. The programmable processor can include the transmission logic.

In another aspect, a method and computer program product are provided that include generating first-priority data and second-priority data. The first-priority data is placed in a first data buffer, and the first data buffer is for use with only first-priority data. The second-priority data is placed in a second data buffer, and the second data buffer is for use with only second-priority data. The first-priority data and the second-priority data are transmitted from the first and second data buffers over the data link. The first-priority data is transmitted preferentially over the second-priority data.

Particular implementations may include one or more of the following features. Third-priority data can be generated, where the first-priority data is high-priority data, the second-priority data is low-priority data, and the third-priority data is medium-priority data. The third-priority data can be placed in a third data buffer, and the third data buffer can be for use with only third-priority data. The third-priority data can be transmitted from the third data buffer over the data link. The first-priority data can be transmitted preferentially over the third-priority data, and the third-priority data can be transmitted preferentially over the second-priority data. A messaging protocol can be identified, and transmitting preferentially can include transmitting preferentially in accordance with the messaging protocol. Transmitting the first-priority data preferentially over the second-priority data can include transmitting any available first-priority data before any available second-priority data. Transmitting the first-priority data preferentially over the second-priority data can include allocating more transmit slots to available first-priority data than to available second-priority data. The first-priority data can include time-critical messages. The second-priority data can include at least one of non-critical status information and error-logging information.

Particular embodiments can be implemented to realize one or more of the following advantages. Multiple independent streams of data assigned to different priority levels can be transmitted throughout a system using point-to-point serial connections. A same messaging protocol can be used for multiple communication links having different types and speeds in the system.

The details of one or more embodiments of the invention are set forth in the accompanying drawings and the description below. Other features, aspects, and advantages of the invention will become apparent from the description, the drawings, and the claims.

BRIEF DESCRIPTION OF THE DRAWINGS

FIG. 1A is a block diagram of a system that includes multiple nodes connected by links.

FIG. 1B is a block diagram of a single node.

FIG. 1C is a flowchart of a transmit process performed at a node.

FIG. 2 is a diagram of the structure of a hardware-level data packet.

FIG. 3 is a timing diagram of packet transmission between nodes.

FIG. 4 is a timing diagram of an error recovery scenario.

FIG. 6 is a flowchart of a process performed at a node.

FIG. 7 is a diagram of the structure of a message.

FIG. 8 is a diagram of the structure of a message.

Like reference numbers and designations in the various drawings indicate like elements.

DETAILED DESCRIPTION

Figure 5:
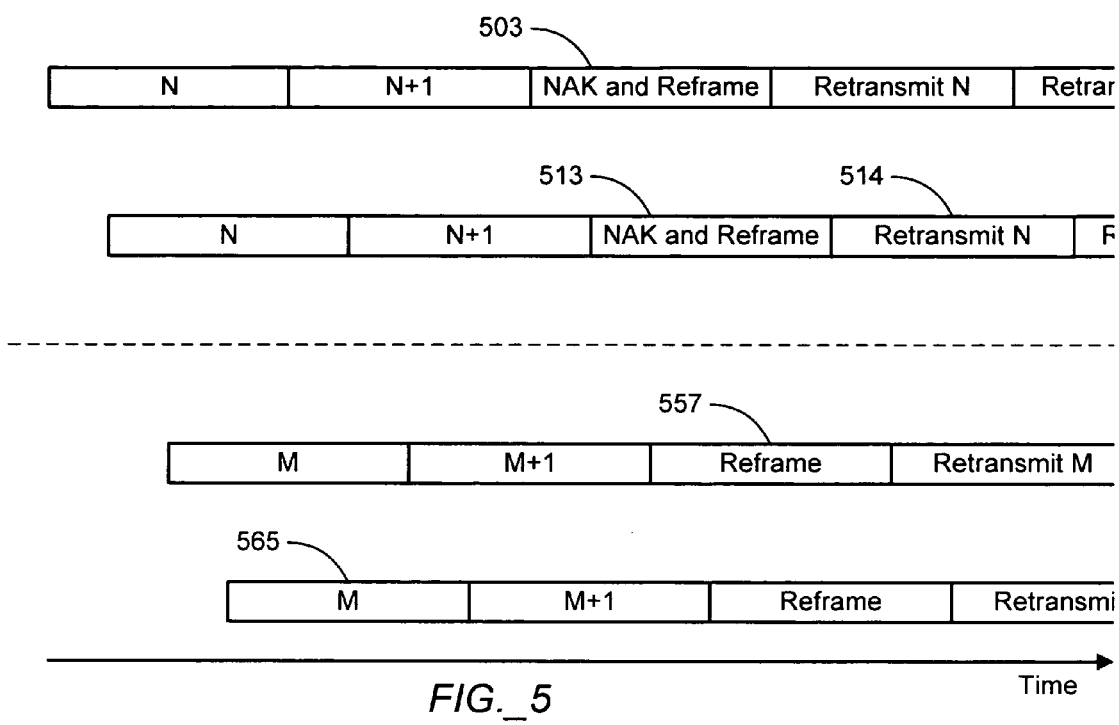
FIG. 5 is a timing diagram of an error recovery scenario.

A method and architecture (including data structures) for communicating data messages in a system is described that allows messages having different priorities to be transmitted over a single serial path between two system nodes. Nodes can include, for example, computers, programmable processors, field-programmable gate arrays (FPGAs), or other data processing apparatus. The data messages (e.g., software messages) can be transmitted using any suitable link layer. In this application, an implementation is described that transmits a substantially continuous stream of full-duplex serial data between two nodes. The data messages are divided into one or more segments, each of which is transmitted in a fixed-length hardware-level packet. The data messages typically will be referred to simply as "messages" in this application.

The fixed-length packets are continuously transmitted between two nodes, regardless of whether message data is available to transmit. When no data is available to transmit, the data field of a packet can be filled with "filler" data that can be discarded at the receiving node. The transmitted packets include acknowledgements of previously received packets, and a transmitting node will transmit a first packet and begin transmitting at least one subsequent packet before receiving an acknowledgement of the first packet from the receiving node. The transmission and receipt of packets at a node are interlocked, as will be described in more detail below.

As shown in FIG. 1A, message data from a first node 110 can be transmitted to multiple destination nodes—for example, a second node 120, a third node 130, and a fourth node 140—by multiplexing the data on a serial link. Nodes between the first node 110 and a particular destination node can route the data. The first node 110 can transmit data for the second node 120 over a first link 125. The first node 110 also can transmit data for the third node 130 over the first link 125 to the second node 120, and the second node 120 can route the data to the third node 130 over a second link 135. Likewise, the first node 110 can transmit data for the fourth node 140 over the first link 125, and the second node 120 can route the data to the fourth node 140 over a third link 145.

The designation of a destination node can be handled, in one implementation, in the message data being transmitted. In this implementation, the second node 120 typically processes at least part of a message being sent from the first node 110 before sending hardware-level packets containing portions of the message to the destination node. If the second node 120 is itself the destination node, the message need not be transmitted any further.

In some systems, communications occur more frequently between the first node 110 and the third node 130 and the fourth node 140 than communications between the third node 130 and the fourth node 140 occur. In such systems, the first link 125 can be a higher-speed link than the second link 135 or the third link 145 to provide sufficient capacity for the greater volume of data that passes over the first link 125.

The nodes 110, 120, 130, and 140 can include one or more hardware data buffers 152-164 that receive messages and hold the messages until software executing on the respective node or on a data processing apparatus in communication with the respective node is ready to receive the messages. The hardware data buffers 152-164 also can receive messages from a software application associated with the respective node and hold the messages until the node is ready to transmit the messages.

As shown in FIG. 1B, one implementation of a node 170 includes a message manager 174, transmit/receive logic 178, transmit buffer 182, and receive buffer 184. The transmit buffer 182 and receive buffer 184 each are divided into portions (e.g., creating separate transmit buffers 182-1, 2, 3 and receive buffers 184-1, 2, 3, respectively) designated for different priorities of messages, as will be explained below. In one implementation, plural transmit buffers 182 are provided, one or more for each priority level. For the purposes of the discussion below, reference will be made to an implementation that includes plural transmit and receive buffers. Other configurations are possible. Each buffer is individually addressable so that the message manager 174 and the transmit/receive logic 178 can place bytes into any buffer or read bytes out of any buffer independently of the other buffers.

The message manager 174 can place a message or portion of a message into any of the transmit buffers 182-1, 2, 3. In one implementation, the message manager 174 places high-priority messages in a high-priority transmit buffer 182-1, medium-priority messages in the medium-priority transmit buffer 182-2, and low-priority messages in the low-priority transmit buffer 182-3. Although three priority levels are shown in this example, fewer (e.g., 2) or more priority levels can be assigned and processed by the system.

The transmit/receive logic 178 transmits messages or portions of messages from the transmit buffer 182 over serial link 186 in accordance with a messaging protocol. The messaging protocol can provide a prescribed quality of service for messages of different priority levels (e.g., based on which buffer the message is assigned to) creating channels of communication between the respective nodes. In one implementation, each channel has a different priority level. The transmit/receive logic 178 can automatically transmit a portion of a message once enough data is written into a buffer to fill a hardware-level packet. That is, message transmission can be performed as data becomes available and need not wait until an entire message is written into the buffer.

The messaging protocol can be implemented to provide a selectable (e.g., user or otherwise defined) quality of service. In one implementation, when messages having differing priorities are available for transmission (e.g., messages are present in the high and medium priority transmit buffers 182-1 and 182-2), the transmit/receive logic 178 transmits a highest-priority message or portion of a message preferentially over other lower-priority messages. For example, the transmit/receive logic 178 transmits a message from the high-priority transmit buffer 182-1 before a message or portion of a message from the medium-priority 182-2 or low-priority 182-3 transmit buffers is sent. Likewise, messages or portions of messages are transmitted from the medium-priority transmit buffer 182-2 before messages stored in the low-priority transmit buffer 182-3.

In another implementation, the transmit/receive logic 178 can implement a messaging protocol that multiplexes messages. In this implementation, the transmit/receive logic 178 defines slots for transmission between the nodes. The slots can be filled in accordance with the proscribed quality of service. For example, available messages or portions of messages in the high-priority transmit buffer 182-1 can be allocated more transmit slots than available messages or portions of messages in the medium-priority 182-2 or low-priority 182-3 transmit buffers.

In yet another implementation, the transmit/receive logic 178 can implement a messaging protocol that services (e.g., transmits) messages or portions of messages that are available in the transmit buffer 182 in a round-robin manner, but more high-priority transmit buffers (e.g., 4) are provided than medium-priority buffers (e.g., 2) or low-priority buffers (e.g., 1).

The transmit/receive logic 178 also receives messages and portions of messages from the serial link 186 and places the messages or portions of messages into the appropriate buffer in the receive buffer 184. The transmit/receive logic 178 uses a channel indication in the hardware-level packets transmitted over the serial link 186 (discussed below) to determine which priority level a given message or portion thereof belongs to. In one implementation, the transmit/receive logic 178 passes received messages to the message manager 174 and the receive buffer 184 is not used. In an alternative implementation, received messages are not segregated according to priority in the receive buffer 184.

The message manager 174 and the transmit/receive logic 178 each can be a computer, a programmable processor, an FPGA, engine, or another data processing apparatus. Although the message manager 174 and transmit/receive logic 178 are illustrated as separate components, they can be combined into a single component. Transmit/receive logic 178 also can be divided into separate transmit logic and receive logic elements.

The transmit buffer 182 and the receive buffer 184 can be first-in first-out (FIFO) data buffers or can be circular buffers with read and write pointers. The transmit buffer 182 and the receive buffer 184 can each be implemented on separate devices (e.g., separate integrated circuits) or can be implemented on portions of a single device. In one implementation, all of the components of node 170, including the buffers, are implemented in a single FPGA.

FIG. 1C shows a process 102 for transmitting messages having different priorities. In the example, three message priorities are included: high-, medium-, and low-priority messages. As an initial step, messages for transmit are identified and typed (step 190) (e.g., by software executing on the message manager 174 in FIG. 1B). The messages are placed in respective transmit buffers according to type (step 192), high-priority messages in a high-priority transmit buffer, medium-priority messages in a medium-priority transmit buffer, and low-priority messages in a low-priority transmit buffer. A messaging protocol is identified (e.g., transmit/receive logic 178 determines a quality of service for each type of message (step 193)). The messages are then transmitted (e.g., by transmit/receive logic 178) in accordance with the identified message protocol (e.g., the high-priority messages are transmitted preferentially over the medium- and low-priority messages (step 194) and the medium-priority messages are transmitted preferentially over the low-priority messages (step 196)). Possible ways in which messages can be transmitted preferentially were discussed above in the context of transmit/receive logic 178.

As shown in FIG. 2, a fixed-length packet 200 of one implementation can include multiple bytes 201-240. While a 40-byte packet is shown, the fixed-length packet can be other lengths. In the implementation shown, control information is placed in 8 of the 40 bytes, and data is placed in the remaining 32 bytes. The first byte 201 is a synchronization field that can be used to maintain byte framing at a node that receives the packets. An additional synchronization byte can periodically be added to a packet (e.g., once every 128 packets) to compensate for clock drift between nodes. The second byte 202 is an acknowledgement field that indicates whether the last packet received by the node transmitting packet 200 was received correctly (e.g., included valid error-checking information). The second byte 202 can be set to one value (e.g., 0×AC) to indicate an acknowledgement (ACK) that the last packet was received correctly and to the inverse value (e.g., 0×53) to indicate that the last packet was not received correctly (no acknowledgement, or NAK). In one implementation, any value other than the acknowledgement value can be interpreted as no acknowledgement. In this implementation, if the NAK value is the inverse of the ACK value, an 8-bit error is required to transform a transmitted NAK into an ACK.

The third byte 203 is a response field that contains multiple control bits, such as a test-mode bit that indicates the system is in a diagnostic test mode and an XOFF bit for each of multiple message channels (e.g., low-, medium-, and high-priority channels). The control bits can also include a retransmission bit that when set indicates that the packet 200 is a retransmission of an earlier packet. One or more of the control bits also can be fault bits, which indicate that an error has occurred in the system.

The fourth byte 204 is a header field. The header field can include multiple subfields, such as a channel-select subfield and a command subfield. The channel-select subfield is used to indicate on which priority channel the data in the packet 200 is being transmitted. The command subfield can include instructions to flush buffers and restart a message stream. The command subfield can include instructions requesting that particular data be sent over the hardware channel or codes to identify such data. The command subfield also can be used to synchronize the system. For example, at the beginning of a synchronization cycle, a packet that contains the synchronization command can be sent, enabling subsystems within the system maintain synchronization (e.g., to within 10 microseconds). The fifth byte 205 is a sequence number field that contains a hardware-level packet sequence number that can be used by a receiving node to detect transmission errors. The sixth byte 206 through the 37$^{th}$ byte 237 belong to a data field that holds 32 bytes of data, such as a message or portion of a message.

The 38$^{th}$ byte 238 is an end-of-packet field that can specify how many of the bytes in the data field correspond to a message and how many bytes are filler bytes. The end-of-packet field also can include an end-of-message indicator bit that is set when the bytes in the data field end a message. The end-of-message indicator bit can trigger an interrupt at the receiving node. The 39$^{th}$ byte 239 and 40$^{th}$ byte 240 are part of an error-checking field that can contain, in one implementation, a 16-bit CRC value (e.g., computed using the CCITT 16-bit CRC algorithm). When a node receives a packet, the node can use the error-checking field to determine whether an error occurred while the packet was being transmitted or received.

The structure of the packet 200 allows fault reaction logic (FRL) signals that indicate a fault in a node to be communicated in multiple ways. For example, FRL signals can be transmitted in packet control information (e.g., in the control bits of the response field of packet 200), and/or in messages. Transmitting FRL signals directly in packet control information allows fault information to be transmitted very quickly system wide and to be handled at a very low level. A system-wide fault signal can be propagated without software intervention, and fault reaction hardware can put the system in a safe state when a fault signal is received. Once the problem that caused the fault has been solved (e.g., by the intervention of a human operator), the fault signal can be cleared and the system can return to an operational state. When the fault signal is cleared, the FRL signal indicating a fault typically is not transmitted in the packet control information until another fault occurs. Redundant FRL signals can be transmitted in high- and medium-priority messages.

The described hardware packet structure allows messages to be sent on a single channel or on multiple channels that are multiplexed on a serial link. The channel on which a particular message is being sent is indicated by the channel select subfield in the packet 200. Time-critical messages can be transmitted on the high-priority channel, while relatively unimportant messages can be transmitted on the low-priority channel.

An example of a system in which transmitting messages having different priority levels is beneficial is a robot-assisted surgical system. Such a system can include multiple robotic arms that hold surgical instruments or devices (e.g., laparoscopes, endoscopes, lights, cameras, and insufflators), some of which may be inside a patient. The robotic arms typically are manipulated remotely by a surgeon who is seated at a control console. Communications between the controls that the surgeon operates and the nodes that control the robotic arms can use the methods, systems, and apparatus described in the current disclosure. Commands from the surgeon to control the movement of a robotic arm typically are transmitted on a high-priority channel so that the delay is minimized between the issuance of a command and the resulting movement. Responses from the robotic arm (e.g., measurements of the arm's actual movement from sensors in the arm) also can be transmitted on the high-priority channel to allow rapid feedback on the arm's response to the commands. Asynchronous system messages such as non-critical status information and error-logging information can be transmitted on the medium- or low-priority channel.

The XOFF bits in the third byte 203 control the flow of data in the channels. Each node can include multiple hardware buffers that receive messages transmitted on a respective one of the multiple channels. For example, high-priority messages are stored in a high-priority buffer and low-priority messages are stored in a low-priority buffer. When a first node that transmits the packet 200 sets an XOFF bit in the packet 200, the first node is instructing a second node that receives the packet 200 to stop transmitting data to the first node on the respective data channel. The first node's hardware can automatically set an XOFF bit for a data channel, for example, when a buffer into which the first node places messages from that data channel is becoming full. In one implementation, a threshold for when a node sets the XOFF bit for a given channel is set equal to the size of the respective channel's receive buffer in the node (e.g., 512 words) minus 32 words (4 packets). The 32-word margin gives the receiving node time to receive and act on the XOFF signal with a margin for error. Other threshold levels are possible. The first node's hardware also can set the XOFF bit for the data channel when a large number (e.g., 12) of messages are in the receive buffer. The hardware can automatically clear the XOFF bit for the data channel once packets or messages are removed from the buffer. Each priority channel can have a respective receive buffer in a node. Because the XOFF bits are transmitted in every packet, the error-checking field applies to the XOFF bits and guards against corruption of the XOFF bits.

Multiple channels of communication can be made available in the link layer using the channel-select subfield described above. For example, a hardware channel and high-, medium-, and low-priority channels can be implemented. Messages can vary in length (e.g., between 3 and 128 words) and can be transmitted in one or more packets, depending on the length of the message. System hardware can fragment messages into multiple packets at a transmitting node and defragment the messages at a receiving node. If a message does not fill the data portion of a packet, filler data can be inserted into the remainder of the data portion. Transmit and receive buffers for the messages can be implemented in hardware. For example, a node can include hardware transmit and receive buffers for each channel (e.g., high-, medium-, and low-priority channels). In one implementation, transmit and receive buffers for the channels are 1.5 times a maximum message size.

FIG. 3 shows a conceptual timing diagram for communication between two nodes using packets such as those discussed in the context of FIG. 2. Packets 301-304 are transmitted sequentially from a primary node to a secondary node. Packets 311-314 are received at the secondary node and correspond to the packets 301-304, although the packets 311-314 may be corrupted versions of the respective packets 301-304 if transmission errors occurred. The receipt of the packets 311-314 is delayed in time relative to the transmission of the packets 301-304 because of the finite propagation time of the packet along a link. In the example shown in FIG. 3, the propagation time of the packet is less than the duration of the packet (the amount of time required by the primary node to transmit the packet).

The secondary node transmits packets 355-358 to the primary node. Packets 365-368 are received at the primary node after a delay and correspond to the packets 355-358. The Packet 356 includes an acknowledgement field that applies to the packet 301. If the packet 311 (which corresponds to packet 301) was received correctly at the secondary node, the packet 356 includes an ACK for packet 301. If the packet 311 was not received correctly, the packet 356 includes a NAK. The packet 357 includes an acknowledgement field corresponding to the packet 302. Similarly, the packet 303 includes an acknowledgement field that indicates whether or not the packet 365 was received correctly at the primary node, and the packet 304 includes an acknowledgement field for the packet 366.

In one implementation, the secondary node does not begin transmitting packets until a first acknowledgement field is received from the primary node. For example, the secondary node does not begin transmitting the packet 355 until the secondary node receives the acknowledgement field in the packet 311. To facilitate initial synchronization between the primary and secondary nodes, the two nodes can transmit several sequential synchronization bytes to each other before the primary node transmits the packet 301.

FIG. 3 illustrates a case in which there is a two-packet "pipeline" between the primary and secondary nodes. The packet 356 contains an acknowledgement field for the packet 301. If the acknowledgement field contains an ACK, the primary node transmits the packet 303. If, however, the acknowledgement field of the packet 356 contains a NAK, the primary node can reframe and retransmit the packets 301 and 302. In this implementation, two packets are retransmitted when a NAK is received for the first of the two packets in order to resynchronize the system. If the first of the two packets was not received correctly, the second packet can be retransmitted without checking whether the second packet was received correctly the first time it was transmitted. In a situation where the error in the first packet was caused by loss of synchronization between the two nodes, the second packet would likely contain errors, so the second packet is retransmitted preemptively. The node that transmitted the NAK also will retransmit the last two packets that it transmitted before transmitting the NAK. FIG. 3 is described as having a two-packet pipeline between the primary and secondary nodes because an acknowledgement field is received for a given packet only after another packet has been transmitted. The round-trip time between the primary and secondary nodes is equal to or slightly less than the time required to transmit one packet—that is, the primary node will begin receiving the packet 365 before the primary node has finished transmitting the packet 301. The round-trip time typically depends on the propagation delay over a link and the processing time at a node. Longer round-trip times (longer in absolute time or in time relative to the packet duration) also can be used in a system and can result in a pipeline that is deeper than two packets.

Packets are transmitted substantially continuously between the primary and secondary nodes, regardless of whether there are messages to place in the data fields of the packets. The packets are transmitted in an interlocked manner, as shown in FIG. 3. The interlocked transmission of fixed-length packets causes a fixed phase offset between the packets received at a node and the packets transmitted by the node. The node receives a packet from a remote node that contains an acknowledgement of error-free receipt of a previously transmitted packet a predetermined amount of time after the transmission of the previously transmitted packet. The continuous transmission of interlocked packets allows for high-bandwidth, low-latency communications with precise synchronization between nodes. In addition, the continuous transmission of packets allows the system to calculate the bit error rate (BER) of a connection between nodes accurately and substantially continuously.

As shown in FIG. 4, when the secondary node receives a packet 411 from the primary node and determines that a transmission error occurred that caused the data in the packet 411 to become corrupted, the secondary node finishes transmitting a packet and, instead of transmitting a next packet, transmits a NAK and reframing sequence 456 to the primary node. The reframing sequence 456 is transmitted to reestablish synchronization between the primary and secondary nodes, because one reason that the packet 411 may have been corrupted is that synchronization between the primary and secondary may have been diminished or lost. The reframing sequence can consist of alternating synchronization fields and link fields, where the link field can be a predetermined code such as 0xA3. In one implementation, four link bytes must be received before a node is considered reframed. The primary node receives a NAK and reframing sequence 466 and transmits a reframing sequence 403. After the primary node has transmitted the reframing sequence 403, the primary node resends the last packets that were transmitted before receiving the NAK. In the case of an N-packet pipeline, the last N packets are resent. Once the secondary node receives an ACK in a first retransmitted packet 414, the secondary node also begins retransmitting packets.

As shown in FIG. 5, when the primary node receives a packet 565 from the secondary node and determines that a transmission error occurred that caused the data in the packet 565 to become corrupted, the primary node sends a NAK and reframing sequence 503 to the secondary node. The secondary node receives a NAK and reframing sequence 513 and sends a reframing sequence 557. After the primary node has transmitted the NAK and reframing sequence 503, the primary node resends the last packets that were transmitted before receiving the corrupted packet. Once the secondary node receives an ACK in a first retransmitted packet 514, the secondary node also begins retransmitting packets.

An error counter can keep track of the number of hardware transmission errors that occur in a node. An interrupt can be enabled when the counter reaches a threshold. In one implementation, the error counter can be read by software in the node, and the software can set the interrupt threshold. Error detection and correction can be handled at a very low level in this system, and a software layer operating on top of the described link layer need not implement additional error detection and correction.

FIG. 6 illustrates a process 600 performed at a node in one implementation. The node begins receiving a first packet (step 610) and receives an acknowledgement field in the first packet (step 615). The node determines whether the acknowledgement field is an ACK or a NAK (step 620). If the acknowledgement field is a NAK, the node transmits a reframing sequence (step 625) and retransmits the packet that the received NAK corresponded to along with any packets that were transmitted after that packet (step 630). If the acknowledgement field is an ACK, the node begins transmitting a second packet (step 635) and checks the first packet for errors (step 640), for example, by verifying a CRC value in the packet. If errors were detected in the first packet, the node finishes transmitting the second packet (step 645) and transmits a NAK and reframing sequence (step 650).

If no errors were detected in the first packet, the node determines whether a fault bit was set in the first packet (step 655). If a fault bit was set, the node is put into a fault mode or safe state (step 660). If the fault bit was not set, or once the node is put into a fault mode, the node finishes transmitting the second packet (step 665) and begins transmitting a third packet (step 670).

FIG. 7 shows a message 700 that can be transmitted over the link layer described in the context of FIGS. 2-6 to communicate between nodes in the system. The message 700 also can be transmitted over other connections, such as USB, RS-232, or IEEE 802.3 (Ethernet). The same message 700 can be transmitted over each type of connection, wrapped in a connection-specific wrapper as appropriate. For example, a message that is transmitted in the sixth byte 206 through the 37$^{th}$ byte 237 of packet 200 (FIG. 2) is a message 700 wrapped in a wrapper that will be described below in the context of FIG. 8. Because a common format is used throughout the system for the message 700, the message 700 can be transmitted to any node in the system without translation.

The message 700 includes multiple bytes 701-708. The first six bytes 701-706 of the message 700 form a header and the last bytes 707-708 form a message body. The message body in the last bytes 707-708 can vary in length (bytes between byte 707 and byte 708 are not shown). The first byte 701 of the header includes a checksum field for the following bytes. The second byte 702 includes a command field that can include, for example, a synchronization command or a configuration-checking command. A node can respond to a command issued by another node (e.g., to report the status of the command's execution), and the command field can include a response bit. The responding node can set the response bit of the command field in a response message sent to the node that issued the command. The response bit indicates that the message is a response to a command and does not include a new command.

The third byte 703 in the message 700 includes a source field that indicates from which the node the message 700 was transmitted. The fourth byte 704 includes a destination field that indicates to which node (or nodes) the message 700 should be transmitted. The fifth byte 705 includes a status field. A responding node can include information about the execution of a command in the status field (e.g., indicating success or failure) when sending a response message. The sixth byte 706 includes a length field that indicates how long the body of the message 700 is.

As shown in FIG. 8, a message 800 for transmission using the link layer described above includes multiple bytes 801-810. The first four bytes 801-804 form a header, the last four bytes 807-810 form a tail, and the middle bytes 805-806 form a body that contains the message 700 (FIG. 7). The first byte 801 of the header includes a length field that indicates how long the body of the message is. The second byte 802 of the header includes a type field that can specify a type of the message. The third byte 803 of the header includes a source field that indicates from which the node the message 800 was transmitted. The fourth byte 804 of the header includes a destination field that indicates to which node (or nodes) the message 800 should be transmitted.

The middle bytes 805-806 can vary in length (bytes between byte 805 and byte 806 are not shown) and contain the message 700 (FIG. 7). The first byte 807 of the tail can be a padding byte that is reserved for future use. The second byte 808 of the tail can be a sequence number field. The third and fourth bytes 809-810 of the tail can be a checksum field for the header and body of the message 800.

The sequence number field in the second byte 808 of the tail can include a sequence number for the message 800 that is specific to the priority channel on which the message 800 is being transmitted. That is, the system can assign sequence numbers to messages transmitted on a given priority channel independently of the other priority channels. The sequence number also can depend on which node forms and begins the transmission of the message 800. In this way, each node in the system can have a different beginning sequence number for each priority channel on the node. The sequence number for a given node and priority channel is incremented after a message is transmitted successfully from that particular node on that particular priority channel.

The checksum field in the third and fourth bytes 809-810 of the tail can be a summation of the bytes in the header and body. The checksum field can be used to detect errors in the message 800. The body of the message 800 also can include a CRC checksum for more robust error detection.

When the system is powered up, software in a master node (e.g., at the surgeon's console in a robot-assisted surgical system) can assign node IDs to each node in the system that will be used to identify the respective node in the source and destination fields of the message 800. One or more special IDs can be reserved and used to indicate that a message which includes that special ID in the destination field is to be broadcast to multiple nodes.

The software in the master node can query the other nodes in the system to determine what version of software the other nodes are running. If a node in the system is running an unexpected version of software (e.g., the version does not match the master node's version or does not match required version information stored in the master controller), a fault can be triggered, and the nodes of the system can be put into a safe state until an operator loads the correct version of software onto the node or replaces the node with a different node having the correct version of software installed.

When a fault occurs in the system, the cause of the fault typically is stored in an error log on the node where the fault occurred. Information on the cause of the fault typically also is transmitted to the master node to be logged there as well.

In one implementation, a node can include a port for communicating using the link layer described above, a USB port, an RS-232 port, and an Ethernet port. Some or all of the ports can be used to communicate with other nodes, and some or all of the ports can be used to connect equipment that tests or updates the system. When equipment that tests or updates the system is connected to a port, the system may require that the equipment provide a password for security.

Messages can be used for system maintenance and updating. For example, messages can be used to transmit software updates to a node from another node or from update equipment (e.g., a laptop computer) coupled to one of the nodes. Diagnostic or update equipment that is coupled to a node can communicate with that node and also can communicate with other nodes in the system by using the node to which the equipment is connected to forward messages to the desired node (e.g., by specifying the desired node in the destination field of the message 800). The use of a common format for the message 700 throughout the system allows the diagnostic or update equipment to communicate with any node in the system in a straight-forward manner.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, i.e., one or more modules of computer program instructions encoded on a computer-readable medium for execution by, or to control the operation of, data processing apparatus. The computer-readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. For example, the actions recited in the claims can be performed in a different order and still achieve desirable results. The methods, systems, and apparatus described above can be used with various physical transport mechanisms, including fiber optics (e.g., operating at 160 Mb/sec), low-voltage differential signaling (e.g., operating at 122 Mb/sec), source synchronous serial, and asynchronous backplane wires. In one implementation, corrupt packets need not be retransmitted when the packets contain data that can tolerate errors. For example, occasional glitches in a video or audio stream are acceptable. Error detection and reframing can still be used in this implementation to allow fast hardware-implemented recovery from framing errors.

What is claimed is:

1. A robot-assisted surgical system comprising:
   a plurality of nodes, each node coupled to at least one other node with a serial data link, the serial data link being configured to transfer data having different priority types between the respective nodes, each node including:
   a programmable processor operable to execute instructions;
   a first data buffer coupled to the programmable processor, the programmable processor being operable to transfer first-priority data received by the node over a first serial data link to the first data buffer responsive to the instructions, the first data buffer being for use with only the first-priority data, the first-priority data being messages having been assigned a first priority type and including surgical control commands of the robot-assisted surgical system;
   a second data buffer coupled to the programmable processor, the programmable processor being operable to transfer second-priority data received by the node over the first serial data link to the second data buffer responsive to the instructions, the second data buffer being for use with only the second-priority data, the second-priority data being messages having been assigned a second priority type and including non-critical system communications of the robot-assisted surgical system; and
   transmission logic coupled to the first and second buffers and to the serial data link, the transmission logic being operable to transmit the first-priority data preferentially over the second-priority data over the serial data link in accordance with a messaging protocol.

2. The robot-assisted surgical system of claim 1, wherein:
   the first-priority data includes commands to control the movement of a robotic arm; and
   the second-priority data includes at least one of non-critical status information and error-logging information.

3. The robot-assisted surgical system of claim 1, further comprising:
   a third data buffer coupled to the programmable processor, the programmable processor being operable to transfer third-priority data to the third data buffer responsive to the instructions, the third data buffer being for use with only the third-priority data, wherein the first-priority data is high-priority data, the second-priority data is low-priority data, and the third-priority data is medium-priority data.

4. The robot-assisted surgical system of claim 3, wherein:
   the messaging protocol requires that the transmission logic transmit the first-priority data from the first data buffer preferentially over the second-priority data from the second data buffer.

5. The robot-assisted surgical system of claim 4, wherein:
the messaging protocol further requires that the transmission logic transmit the first-priority data from the first data buffer preferentially over the third-priority data from the third data buffer.

6. The robot-assisted surgical system of claim 5, wherein:
the messaging protocol further requires that the transmission logic transmit the third-priority data from the third data buffer preferentially over the second-priority data from the second data buffer.

7. The robot-assisted surgical system of claim 4, wherein:
transmitting the first-priority data preferentially over the second-priority data includes transmitting any available first-priority data before any available second-priority data.

8. The robot-assisted surgical system of claim 4, wherein:
transmitting the first-priority data preferentially over the second-priority data includes allocating more transmit slots to available first-priority data than to available second-priority data.

9. The robot-assisted surgical system of claim 1, wherein the programmable processor includes the transmission logic.

10. A method comprising:
providing a robot-assisted surgical system that includes a plurality of nodes, the plurality of nodes including at least a transmit node coupled by a serial data link to a receive node, the serial data link being configured to transfer data having different priority types between the transmit node and the receive node, and at the transmit node:
generating first-priority data and second-priority data, the first-priority data being message data having been assigned a first priority type and associated with critical surgical command messages, and the second-priority data being message data having been assigned a second priority type and associated with non-critical messages;
placing the first-priority data in a first data buffer, the first data buffer being for use with only first-priority data;
placing the second-priority data in a second data buffer, the second data buffer being for use with only second-priority data; and
transmitting the first-priority data and the second-priority data from the first and second data buffers over the serial data link to the receive node, the first-priority data being transmitted preferentially over the second-priority data in accordance with a messaging protocol.

11. The method of claim 10, further comprising, at the transmit node:
generating third-priority data, wherein the first-priority data is high-priority data, the second-priority data is low-priority data, and the third-priority data is medium-priority data;
placing the third-priority data in a third data buffer, the third data buffer being for use with only third-priority data; and
transmitting the third-priority data from the third data buffer over the serial data link, the first-priority data being transmitted preferentially over the third-priority data, the third-priority data being transmitted preferentially over the second-priority data.

12. The method of claim 10, further comprising, at the transmit node:
identifying the messaging protocol, wherein identifying the messaging protocol includes selecting a particular messaging protocol to provide a specified quality of service for messages of different priority types.

13. The method of claim 10, wherein:
transmitting the first-priority data preferentially over the second-priority data includes transmitting any available first-priority data before any available second-priority data.

14. The method of claim 10, wherein:
transmitting the first-priority data preferentially over the second-priority data includes allocating more transmit slots to available first-priority data than to available second-priority data.

15. The method of claim 10, wherein:
the first-priority data includes time-critical messages.

16. The method of claim 10, wherein:
the second-priority data includes at least one of non-critical status information and error-logging information.

17. A computer program product, tangibly embodied on a computer-readable storage medium included in a transmit node of a robot-assisted surgical system, the transmit node coupled by a serial data link to a receive node, the serial data link being configured to transfer data having different priority types between the transmit node and the receive node, the computer-readable medium comprising instructions operable to cause a programmable processor to perform the operations of:
generating first-priority data and second-priority data, the first-priority data being message data having a first priority type and associated with critical surgical command messages and the second-priority data being message data having a second priority type and associated with non-critical messages;
placing the first-priority data in a first data buffer, the first data buffer being for use with only first-priority data;
placing the second-priority data in a second data buffer, the second data buffer being for use with only second-priority data; and
transmitting the first-priority data and the second-priority data from the first and second data buffers over a same serial data link to the receive node, the first-priority data being transmitted preferentially over the second-priority data in accordance with a messaging protocol.

18. The computer program product of claim 17, further comprising instructions operable to perform the operations of:
generating third-priority data, wherein the first-priority data is high-priority data, the second-priority data is low-priority data, and the third-priority data is medium-priority data;
placing the third-priority data in a third data buffer, the third data buffer being for use with only third-priority data; and
transmitting the third-priority data from the third data buffer over the serial data link, the first-priority data being transmitted preferentially over the third-priority data, the third-priority data being transmitted preferentially over the second-priority data.

19. The computer program product of claim 17, further comprising instructions operable to perform the operations of:
identifying the messaging protocol, wherein identifying the messaging protocol includes selecting a particular messaging protocol to provide a specified quality of service for messages of different priority types.

20. The computer program product of claim 17, wherein: transmitting the first-priority data preferentially over the second-priority data includes transmitting any available first-priority data before any available second-priority data.

21. The computer program product of claim 17, wherein: transmitting the first-priority data preferentially over the second-priority data includes allocating more transmit slots to available first-priority data than to available second-priority data.

22. The computer program product of claim 17, wherein: the first-priority data includes time-critical messages.

23. The computer program product of claim 17, wherein: the second-priority data includes at least one of non-critical status information and error-logging information.

24. The method of claim 10, wherein transmitting the first-priority data and second-priority data includes transmitting data as the data is available without waiting for an entire message to be written into a data buffer.

25. The system of claim 1, wherein the programmable processor determines a priority of data using channel indication hardware-level packets.

26. A method of providing patient safety in a robot-assisted surgical system comprising:

receiving multiple messages, at a first node of a plurality of nodes in a robot-assisted surgical system, wherein the multiple messages are generated within the robot-assisted surgical system and are associated with operating the robot-assisted surgical system, the multiple messages being received over a serial data link and including one or more messages having been assigned a different priority type than the priority type of other received messages, the serial data link being configured to transfer messages having different priority types between the respective nodes of the robot-assisted surgical system;

determining a priority for each received message according to the assigned priority type of the message, the determined priority being a first-priority for messages associated with controlling movement of a robotic arm in the robot-assisted surgical system, and the determined priority being a second-priority for messages not associated with controlling movement of a robotic arm in the robot-assisted surgical system; and transmitting the designated first-priority messages preferentially over the designated second-priority messages, the transmitting over the serial data link from the first node in accordance with a messaging protocol.

* * * * *